US011013889B2

(12) United States Patent
Poppe et al.

(10) Patent No.: US 11,013,889 B2
(45) Date of Patent: May 25, 2021

(54) MEDICAL DEVICE WITH SEALING ASSEMBLY

(71) Applicant: BOSTON SCIENTIFIC SCIMED, INC., Maple Grove, MN (US)

(72) Inventors: Kevin Robert Poppe, New Brighton, MN (US); Daniel J. Foster, Lino Lakes, MN (US); Christopher Jay Scheff, Elk River, MN (US); Bradley S. Swehla, Eagan, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 318 days.

(21) Appl. No.: 15/969,817

(22) Filed: May 3, 2018

(65) Prior Publication Data

US 2018/0318546 A1 Nov. 8, 2018

Related U.S. Application Data

(60) Provisional application No. 62/500,990, filed on May 3, 2017.

(51) Int. Cl.
*A61M 25/00* (2006.01)
*A61F 2/966* (2013.01)
(Continued)

(52) U.S. Cl.
CPC .......... *A61M 25/003* (2013.01); *A61F 2/966* (2013.01); *A61M 25/0014* (2013.01);
(Continued)

(58) Field of Classification Search
CPC .. A61M 2025/0681; A61M 2025/0059; A61M 2025/0054; A61M 2025/0052;
(Continued)

(56) References Cited

U.S. PATENT DOCUMENTS 3,674,014 A 7/1972 Tillander
4,798,598 A 1/1989 Bonello et al.
(Continued)

FOREIGN PATENT DOCUMENTS

EP 0778040 A2 6/1997
EP 2455128 A2 5/2013
(Continued)

OTHER PUBLICATIONS

International Search Report and Written Opinion dated Mar. 2, 2018 for International Application No. PCT/US2017/062113.
(Continued)

*Primary Examiner* — Jocelin C Tanner
(74) *Attorney, Agent, or Firm* — Seager, Tufte & Wickhem LLP

(57) ABSTRACT

Medical devices and methods for making and using medical devices are disclosed. An example system for delivering an implantable medical device includes a handle member including a seal assembly, wherein the seal assembly includes a turnbuckle assembly including a stationary member and a cap coupled to the stationary member. Further, the stationary member is coupled to an inner member and the cap is coupled to an exoskeleton disposed along an outer surface of the inner member. Additionally, the cap is designed to shift relative to the stationary member such that the exoskeleton is put in compression.

17 Claims, 9 Drawing Sheets

(51) Int. Cl.
*A61M 25/06* (2006.01)
*A61F 2/962* (2013.01)
*A61F 2/95* (2013.01)

(52) U.S. Cl.
CPC ....... *A61M 25/0054* (2013.01); *A61F 2/9517* (2020.05); *A61F 2/962* (2013.01); *A61F 2002/9665* (2013.01); *A61M 25/0052* (2013.01); *A61M 2025/0059* (2013.01); *A61M 2025/0681* (2013.01)

(58) Field of Classification Search
CPC ............. A61M 25/003; A61M 25/0014; A61F 2002/9665; A61F 2/966; A61F 2/962; A61F 2/9517
See application file for complete search history.

(56) References Cited

U.S. PATENT DOCUMENTS

| | | |
|---|---|---|
| 4,955,384 A | 9/1990 | Taylor et al. |
| 4,985,022 A | 1/1991 | Fearnot et al. |
| 4,998,923 A | 3/1991 | Samson et al. |
| 5,003,989 A | 4/1991 | Taylor et al. |
| 5,095,915 A | 3/1992 | Engelson |
| 5,315,996 A | 5/1994 | Lundquist |
| 5,406,960 A | 4/1995 | Corso, Jr. |
| 5,437,288 A | 8/1995 | Schwartz et al. |
| 5,570,701 A | 11/1996 | Ellis et al. |
| 5,599,492 A | 2/1997 | Engelson |
| 5,746,701 A | 5/1998 | Noone |
| 5,749,837 A | 5/1998 | Palermo et al. |
| 5,769,796 A | 6/1998 | Palermo et al. |
| 5,772,609 A | 6/1998 | Nguyen et al. |
| 5,776,080 A | 7/1998 | Thome et al. |
| 5,833,632 A | 11/1998 | Jacobsen et al. |
| 5,902,254 A | 5/1999 | Magram |
| 5,931,830 A | 8/1999 | Jacobsen et al. |
| 5,951,494 A | 9/1999 | Wang et al. |
| 5,967,984 A * | 10/1999 | Chu ......................... A61B 8/12 600/439 |
| 6,001,068 A | 12/1999 | Uchino et al. |
| 6,017,319 A | 1/2000 | Jacobsen et al. |
| 6,139,510 A | 10/2000 | Palermo |
| 6,176,856 B1 * | 1/2001 | Jandak ................. A61B 18/082 606/29 |
| 6,273,876 B1 | 8/2001 | Klima et al. |
| 6,606,921 B2 | 8/2003 | Noetzold |
| 6,739,787 B1 | 5/2004 | Bystrom |
| 6,918,882 B2 | 7/2005 | Skujins et al. |
| 6,921,397 B2 | 7/2005 | Corcoran et al. |
| 7,055,656 B2 | 6/2006 | Drew |
| 7,074,197 B2 | 7/2006 | Reynolds et al. |
| 7,338,495 B2 | 3/2008 | Adams |
| 7,413,563 B2 | 8/2008 | Corcoran et al. |
| 7,533,906 B2 | 5/2009 | Luettgen et al. |
| 7,540,865 B2 | 6/2009 | Griffin et al. |
| 7,579,550 B2 | 8/2009 | Dayton et al. |
| 7,618,379 B2 | 11/2009 | Reynolds et al. |
| 7,625,364 B2 | 12/2009 | Corcoran et al. |
| 7,780,611 B2 | 8/2010 | Griego et al. |
| 7,784,376 B2 | 8/2010 | Wen |
| 7,824,345 B2 | 11/2010 | Euteneuer et al. |
| 7,841,994 B2 | 11/2010 | Skujins et al. |
| 7,850,623 B2 | 12/2010 | Griffin et al. |
| 7,854,109 B2 | 12/2010 | Zubiate et al. |
| 7,914,466 B2 | 3/2011 | Davis et al. |
| 7,914,467 B2 | 3/2011 | Layman et al. |
| 7,918,080 B2 | 4/2011 | Zubiate et al. |
| 7,993,286 B2 | 8/2011 | Reynolds et al. |
| 8,022,331 B2 | 9/2011 | Reynolds et al. |
| 8,047,236 B2 | 11/2011 | Perry |
| 8,048,004 B2 | 11/2011 | Davis et al. |
| 8,048,060 B2 | 11/2011 | Griffin et al. |
| 8,099,939 B2 | 1/2012 | Zubiate et al. |
| 8,100,031 B2 | 1/2012 | Zubiate et al. |
| 8,105,246 B2 | 1/2012 | Voeller et al. |
| 8,124,876 B2 | 2/2012 | Dayton et al. |
| 8,137,293 B2 | 3/2012 | Zhou et al. |
| 8,157,751 B2 | 4/2012 | Adams et al. |
| 8,182,465 B2 | 5/2012 | Griffin et al. |
| 8,192,422 B2 | 6/2012 | Zubiate et al. |
| 8,197,419 B2 | 6/2012 | Field et al. |
| 8,231,551 B2 | 7/2012 | Griffin et al. |
| 8,257,279 B2 | 9/2012 | Davis et al. |
| 8,292,829 B2 | 10/2012 | Griego et al. |
| 8,317,777 B2 | 11/2012 | Zubiate et al. |
| 8,376,865 B2 | 2/2013 | Forster et al. |
| 8,376,961 B2 | 2/2013 | Layman et al. |
| 8,377,035 B2 | 2/2013 | Zhou et al. |
| 8,397,481 B2 | 3/2013 | Zubiate et al. |
| 8,409,114 B2 | 4/2013 | Parins |
| 8,414,506 B2 | 4/2013 | Reynolds et al. |
| 8,425,408 B2 | 4/2013 | Boulais et al. |
| 8,443,692 B2 | 5/2013 | Zubiate et al. |
| 8,449,526 B2 | 5/2013 | Snyder et al. |
| 8,459,138 B2 | 6/2013 | Zubiate et al. |
| 8,475,366 B2 | 7/2013 | Boulais et al. |
| 8,485,992 B2 | 7/2013 | Griffin et al. |
| 8,535,219 B2 | 9/2013 | Smith et al. |
| 8,535,243 B2 | 9/2013 | Shireman |
| 8,551,020 B2 | 10/2013 | Chen et al. |
| 8,551,021 B2 | 10/2013 | Voeller et al. |
| 8,556,914 B2 | 10/2013 | Vrba |
| 8,608,648 B2 | 12/2013 | Banik et al. |
| 8,622,894 B2 | 1/2014 | Banik et al. |
| 8,636,716 B2 | 1/2014 | Griffin et al. |
| 8,656,697 B2 | 2/2014 | Zubiate et al. |
| 8,677,602 B2 | 3/2014 | Dayton et al. |
| 8,758,268 B2 | 6/2014 | Bown et al. |
| 8,784,337 B2 | 7/2014 | Voeller et al. |
| 8,795,202 B2 | 8/2014 | Northrop et al. |
| 8,795,254 B2 | 8/2014 | Layman et al. |
| 8,821,477 B2 | 9/2014 | Northrop et al. |
| 8,833,197 B2 | 9/2014 | Zubiate et al. |
| 8,845,552 B2 | 9/2014 | Griego et al. |
| 8,864,654 B2 | 10/2014 | Kleiner et al. |
| 8,870,790 B2 | 10/2014 | Davis et al. |
| 8,900,163 B2 | 12/2014 | Jacobsen et al. |
| 8,915,865 B2 | 12/2014 | Jacobsen et al. |
| 8,932,235 B2 | 1/2015 | Jacobsen et al. |
| 8,936,558 B2 | 1/2015 | Jacobsen et al. |
| 8,939,916 B2 | 1/2015 | Jacobsen et al. |
| 8,945,096 B2 | 2/2015 | Zubiate et al. |
| 9,005,114 B2 | 4/2015 | Zubiate et al. |
| 9,011,318 B2 | 4/2015 | Choset et al. |
| 9,023,011 B2 | 5/2015 | Griffin et al. |
| 9,072,874 B2 | 7/2015 | Northrop et al. |
| 9,370,432 B2 | 6/2016 | Bennett et al. |
| 9,375,234 B2 | 6/2016 | Vrba |
| 9,386,911 B2 | 7/2016 | Zubiate et al. |
| 9,387,308 B2 | 7/2016 | Hinchliffe et al. |
| 9,387,309 B2 | 7/2016 | Parodi et al. |
| 9,402,682 B2 | 8/2016 | Worrell et al. |
| 2001/0037141 A1 | 11/2001 | Yee et al. |
| 2003/0069520 A1 | 4/2003 | Skujins et al. |
| 2003/0069521 A1 | 4/2003 | Reynolds et al. |
| 2004/0220499 A1 | 11/2004 | Griego et al. |
| 2004/0243143 A1 | 12/2004 | Corcoran et al. |
| 2005/0080400 A1 | 4/2005 | Corcoran et al. |
| 2005/0090848 A1 | 4/2005 | Adams |
| 2005/0267444 A1 | 12/2005 | Griffin et al. |
| 2006/0111615 A1 | 5/2006 | Danitz et al. |
| 2006/0122537 A1 | 6/2006 | Reynolds et al. |
| 2006/0179966 A1 | 8/2006 | Kuo |
| 2006/0189896 A1 | 8/2006 | Davis et al. |
| 2007/0049902 A1 | 3/2007 | Griffin et al. |
| 2007/0066900 A1 | 3/2007 | O'Keeffe |
| 2007/0083132 A1 | 4/2007 | Sharrow |
| 2007/0100285 A1 | 5/2007 | Griffin et al. |
| 2007/0114211 A1 | 5/2007 | Reynolds et al. |
| 2007/0135734 A1 | 6/2007 | Reynolds et al. |
| 2007/0213812 A1 * | 9/2007 | Webler ............. A61B 17/00234 623/2.11 |

(56) References Cited

U.S. PATENT DOCUMENTS

| | | |
|---|---|---|
| 2007/0233043 A1 | 10/2007 | Dayton et al. |
| 2007/0244414 A1 | 10/2007 | Reynolds et al. |
| 2008/0064989 A1 | 3/2008 | Chen et al. |
| 2008/0077119 A1 | 3/2008 | Snyder et al. |
| 2008/0194994 A1 | 8/2008 | Bown et al. |
| 2008/0205980 A1 | 8/2008 | Zubiate et al. |
| 2008/0245173 A1 | 10/2008 | Schwerin et al. |
| 2008/0262474 A1 | 10/2008 | Northrop |
| 2009/0036833 A1 | 2/2009 | Parins |
| 2009/0043228 A1 | 2/2009 | Northrop et al. |
| 2009/0043283 A1 | 2/2009 | Turnlund et al. |
| 2009/0143768 A1 | 6/2009 | Parodi et al. |
| 2009/0156999 A1 | 6/2009 | Adams et al. |
| 2009/0171151 A1 | 7/2009 | Choset et al. |
| 2009/0312606 A1 | 12/2009 | Dayton et al. |
| 2010/0063480 A1 | 3/2010 | Shireman |
| 2010/0076266 A1 | 3/2010 | Boulais et al. |
| 2010/0080892 A1 | 4/2010 | O'Brien et al. |
| 2010/0145308 A1 | 6/2010 | Layman et al. |
| 2010/0249655 A1 | 9/2010 | Lemon |
| 2010/0286566 A1 | 11/2010 | Griffin et al. |
| 2010/0294071 A1 | 11/2010 | Zubiate et al. |
| 2010/0305475 A1 | 12/2010 | Hinchliffe et al. |
| 2011/0056320 A1 | 3/2011 | Zubiate et al. |
| 2011/0082443 A1 | 4/2011 | Griffin et al. |
| 2011/0152613 A1 | 6/2011 | Zubiate et al. |
| 2011/0178588 A1 | 7/2011 | Haselby |
| 2011/0184241 A1 | 7/2011 | Zubiate et al. |
| 2011/0257478 A1 | 10/2011 | Kleiner et al. |
| 2011/0264191 A1 | 10/2011 | Rothstein |
| 2012/0160537 A1 | 6/2012 | Wen |
| 2013/0123796 A1 | 5/2013 | Sutton et al. |
| 2013/0123912 A1 | 5/2013 | Tung et al. |
| 2014/0235361 A1 | 8/2014 | Forster et al. |
| 2016/0317301 A1 | 11/2016 | Quadri et al. |
| 2018/0140323 A1 | 5/2018 | Foster et al. |

FOREIGN PATENT DOCUMENTS

| | | |
|---|---|---|
| JP | 5575840 B2 | 8/2014 |
| WO | 2006041612 A2 | 4/2006 |
| WO | 2006073581 A2 | 7/2006 |
| WO | 2011133486 A1 | 10/2011 |

OTHER PUBLICATIONS

International Search Report and Written Opinion dated May 22, 2018 for International Application No. PCT/US2018/022371.

International Search Report and Written Opinion dated Jun. 15, 2018 for International Application No. PCT/US2018/022377.

International Search Report and Written Opinion dated Aug. 31, 2018 for International Application No. PCT/US2018/030751.

* cited by examiner

MEDICAL DEVICE WITH SEALING ASSEMBLY

CROSS-REFERENCE TO RELATED APPLICATIONS

This application claims the benefit of priority under 35 U.S.C. § 119 to U.S. Provisional Application Ser. No. 62/500,990, filed May 3, 2017, the entirety of which is incorporated herein by reference.

TECHNICAL FIELD

The present disclosure pertains to medical devices, and methods for manufacturing medical devices. More particularly, the present disclosure pertains to medical devices including a seal assembly designed to prevent fluid leakage within the medical device.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example system for delivering an implantable medical device includes a handle member including a seal assembly, wherein the seal assembly includes a turnbuckle assembly including a stationary member and a cap coupled to the stationary member. Further, the stationary member is coupled to an inner member and the cap is coupled to an exoskeleton disposed along an outer surface of the inner member. Additionally, the cap is designed to shift relative to the stationary member such that the exoskeleton is put in compression.

Alternatively or additionally to any of the embodiments above, wherein the cap is designed to shift distally with respect to the stationary member.

Alternatively or additionally to any of the embodiments above, wherein the exoskeleton includes a plurality of discrete segments engaged with one another, and wherein shifting the cap distally compresses the discrete segments together.

Alternatively or additionally to any of the embodiments above, wherein the cap member is threadedly engaged with the stationary member.

Alternatively or additionally to any of the embodiments above, further comprising a hypotube positioned along the inner member, wherein the hypotube is positioned between the cap and the exoskeleton.

Alternatively or additionally to any of the embodiments above, wherein the cap includes a protrusion configured to engage a proximal portion of the hypotube.

Alternatively or additionally to any of the embodiments above, wherein the cap includes a first seal, and wherein the first seal is disposed along an outer surface of the hypotube.

Alternatively or additionally to any of the embodiments above, wherein the stationary member includes a distal tip region configured to engage a proximal portion of the inner member.

Alternatively or additionally to any of the embodiments above, wherein the stationary member includes a recessed region, and wherein the recessed region is designed to mate with a protrusion in the handle.

Alternatively or additionally to any of the embodiments above, wherein the stationary member is configured to prevent the inner member from shifting with respect to the handle.

Another example system for delivering an implantable medical device includes:
a handle member including a seal assembly, wherein the seal assembly includes:
  a first actuating assembly, wherein the first actuating assembly is configured to receive a deployment sheath;
  a second actuating assembly, wherein the second actuating assembly is configured to receive an actuating shaft; and
  a turnbuckle assembly including a cap and a stationary member;
wherein the turnbuckle is configured to compress an exoskeleton positioned along an inner member;
wherein the inner member is disposed within a portion of the deployment sheath.

Alternatively or additionally to any of the embodiments above, wherein the cap is designed to shift distally with respect to the stationary member.

Alternatively or additionally to any of the embodiments above, wherein the exoskeleton includes a plurality of discrete segments engaged with one another, and wherein shifting the cap distally compresses the discrete segments together.

Alternatively or additionally to any of the embodiments above, wherein the cap member is threadedly engaged with the stationary member.

Alternatively or additionally to any of the embodiments above, further comprising a hypotube positioned along the inner member, wherein the hypotube is positioned between the cap and the exoskeleton.

Alternatively or additionally to any of the embodiments above, wherein the cap includes a protrusion configured to engage a proximal portion of the hypotube.

Alternatively or additionally to any of the embodiments above, wherein the cap includes a first seal, and wherein the first seal is disposed along an outer surface of the hypotube.

Alternatively or additionally to any of the embodiments above, wherein the stationary member includes a distal tip region configured to engage a proximal portion of the inner member.

Alternatively or additionally to any of the embodiments above, wherein the stationary member includes a recessed region, and wherein the recessed region is designed to mate with a protrusion in the handle.

An example method of manufacturing a medical device includes:
coupling a catheter shaft to a handle member, wherein the catheter shaft includes a liner and an exoskeleton disposed over a portion of the liner;
coupling a turnbuckle to the handle member, wherein the turnbuckle includes a cap coupled to the exoskeleton and a stationary member coupled to the liner; and
actuating the turnbuckle to compress the exoskeleton along the liner.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
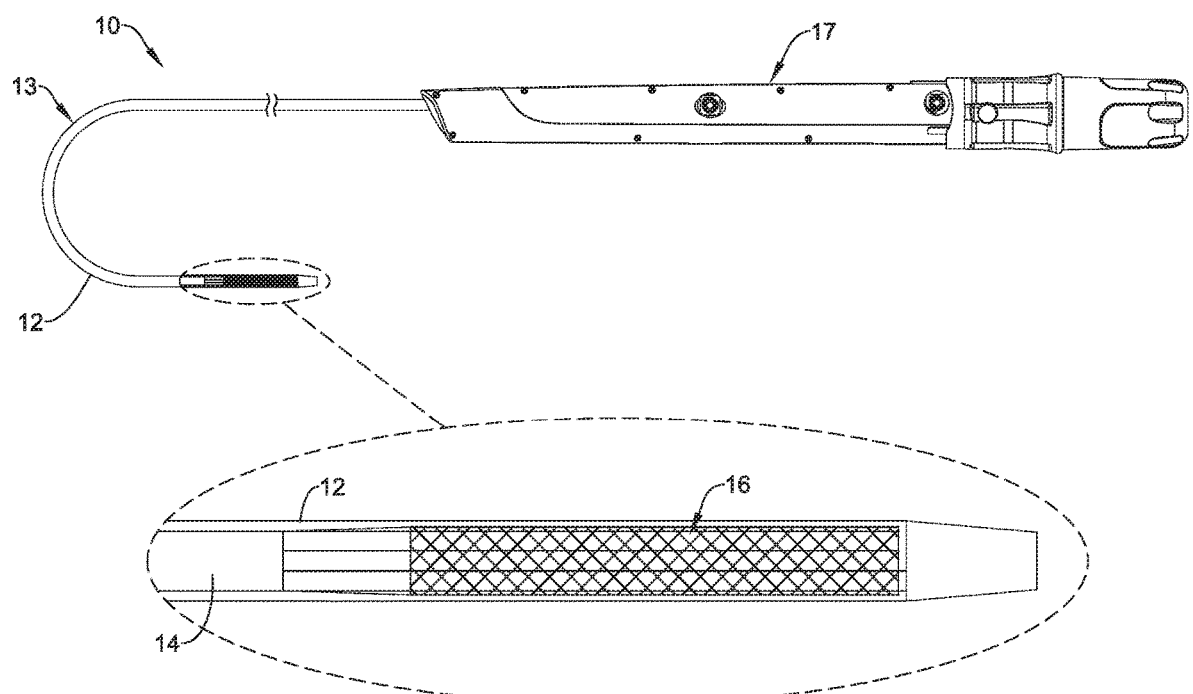
FIG. 1 is a side view of an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the body. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed. For example, therapies have been developed which allow a blocked coronary artery to be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16 (shown in the detailed view of FIG. 1), such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 17 may be disposed at a proximal end of the outer sheath 12 and/or the inner catheter 14 and may include one or more actuation mechanisms associated therewith. In other words, one or more tubular members (e.g., the outer sheath 12, the inner catheter 14, etc.) may extend distally from the medical device handle 17. In general, the medical device handle 17 may be designed to manipulate the position of the outer sheath 12 relative to the inner catheter 14 and/or aid in the deployment of the medical implant 16. Additionally, in some examples the outer sheath 12 of medical device system 12 may include a curved portion 13. While FIG. 1 shows the curve of the outer member 12 lying within the plane of the page, other configurations are contemplated. For example, configurations in which the curve of the outer member extends out of the page are contemplated.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1, for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 17 in order to translate the medical implant 16 into a generally shortened and larger profile "deployed" configuration suitable for implantation within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system (e.g., the medical device system 10) may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

Figure 2:
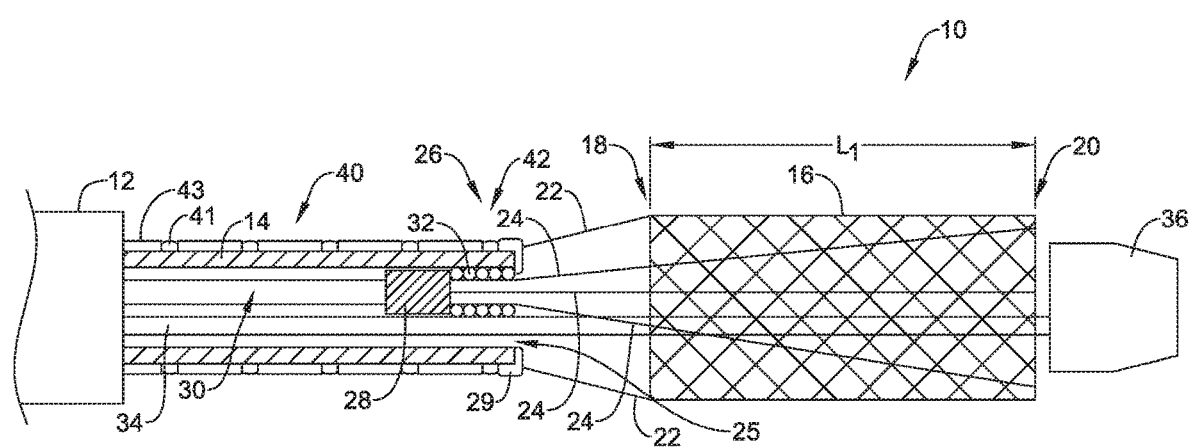
FIG. 2 is a partial cross-sectional view of a portion of an example medical device delivery system.

FIG. 2 illustrates the medical device system 10 in a partially deployed configuration. As illustrated in FIG. 2, the outer sheath 12 of the medical device system 10 has been retracted in a proximal direction to a position proximal of the medical implant 16. In other words, the outer sheath 12 has been retracted (e.g., pulled back) in a proximal direction such that it uncovers the medical device implant 16 from a compact, low-profile delivery position to a partially-deployed position.

In at least some examples contemplated herein, the medical device implant 16 may be designed to self-expand once released from under the outer sheath 12. However, as shown in FIG. 2, the medical device system 10 may be designed such that the implant 16 may be restricted from expanding fully in the radial direction. For example, FIG. 2 shows medical device implant 16 having a partially deployed position denoted as a length "$L_1$."

FIG. 2 further illustrates that in some examples, the implant 16 may include one or more support members 22 coupled to the proximal end 18 of the implant 16. Further, FIG. 2 illustrates that in some examples, the implant 16 may include one or more translation members 24 coupled to the distal end 20 of the implant 16. Additionally, in some examples (such as that illustrated in FIG. 2), the translation members 24 and support members 22 may work together to maintain the implant in a partially-deployed position after the outer sheath 12 has been retracted to uncover the implant 16. For example, FIG. 2 illustrates that the support members 22 may be designed such that the distal end of each of the support members 22 may be coupled to the proximal end of the implant 16 and that the proximal end of each of the support members 22 may be coupled to the distal end of the inner catheter 14. For example, FIG. 2 illustrates that the proximal ends of the support members 22 may be attached to a containment fitting 29 which is rigidly fixed to the distal end of the inner catheter 14. It can be further appreciated that in some instances, the support members 22 may be designed to limit the proximal movement of the proximal end 18 of the implant 16 relative to the distal end of the inner catheter 14.

Additionally, the translation members 24 may be designed to translate in a distal-to-proximal direction such that the translation of the translation members (via operator manipulation at the handle, for example) may "pull" the distal end 20 of the implant closer to the proximal end 18 of the implant 16.

Figure 3:
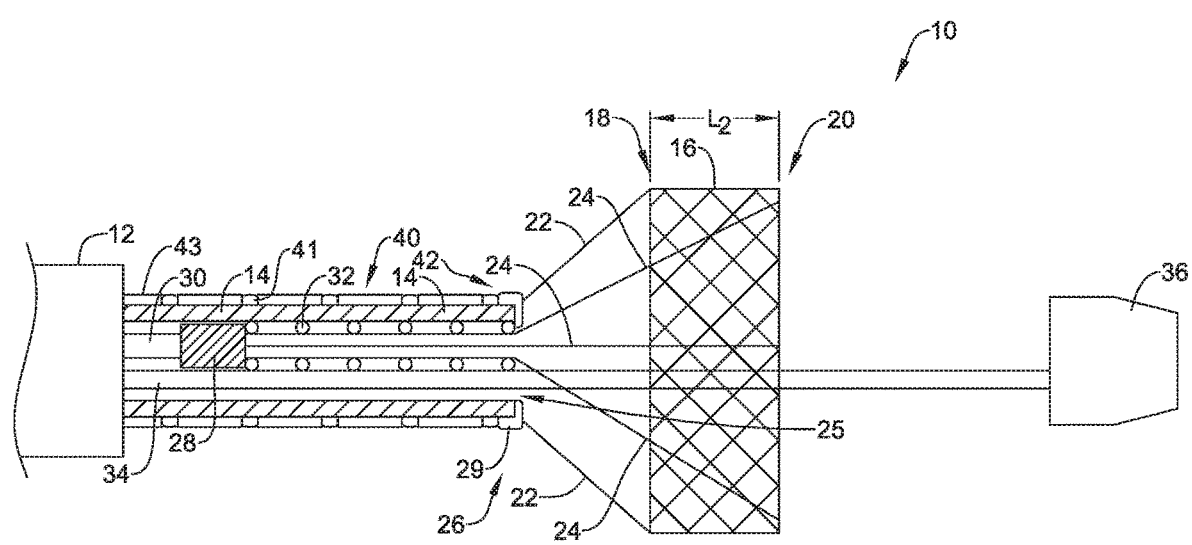
FIG. 3 is a partial cross-sectional view of a portion of an example medical device delivery system.

For example, FIG. 3 illustrates the distal-to-proximal translation of the translation members 24. It can be appreciated that if the support members 22 limit the proximal movement of the proximal end 18 of the implant 16 while the translation members 24 are translated proximally, the implant 16 may both foreshorten (along the longitudinal axis of the implant 16) and also expand radially outward. The foreshortening and radial expansion of implant 16 can be seen by comparing the shape and position of the implant 16 in FIG. 2 to the shape and position of the implant 16 in FIG. 3. The position of the implant 16 shown in FIG. 3 may be described as a fully deployed positioned of the implant 16 (versus the partially deployed positioned of the implant 16 shown in FIG. 2). Further, FIG. 3 depicts the length of the fully deployed implant 16 as "$L_2$", whereby the distance $L_2$ is less than the distance $L_1$ shown in FIG. 2.

Additionally, it can be appreciated that the translation members 24 may be designed to be able extend in a proximal-to-distal direction such that they elongate (e.g., lengthen) the implant 16 (along its longitudinal axis). In other words, the implant 16 may be able to shift between a partially deployed position (shown in FIG. 2) and a fully deployed position (shown in FIG. 3) through the translation (either proximal or distal) of the translation members 24 along the longitudinal axis as the support members 22 limit the movement of the proximal end 18 of the implant 16.

It should be noted that the above description and illustrations regarding the arrangement, attachment features and operation of the support members 22 and the translation members 24 as they engage and function relative to the implant 16 is schematic. It can be appreciated that the design (e.g., arrangement, attachment features, operation, etc.) of the both support member 22 and the translation members 24 as they relate and function relative to the implant 16 may vary. For example, it is possible to design, arrange and operate the translation members 24 and the support members 22 in a variety of ways to achieve the partial and full deployment configurations of the implant 16 described herein.

In some examples, an operator may be able to manipulate the translation members 24 via the handle 17. For example, the handle 17 may include an actuation member designed to control the translation of the translation members 24. FIG. 2 illustrates that the handle member 17 may be coupled to the translation members 24 via an actuation shaft 30 and a coupling member 28. Additionally, FIG. 2 further illustrates that a distal end of actuation shaft 30 may be coupled to the proximal end of the coupling member 28. Further, while not shown in FIG. 2, it can be appreciated that the actuation shaft 30 may extend within the entire length of the inner catheter 14 from the coupling member 28 to the handle member 17.

For purposes of discussion herein, the inner catheter 14 may also be referred to as an inner member or liner 14. The liner 14 may include a number of different features shown in the figures described herein. For example, the liner 14 may include a lumen 25. Further, the translation members 24, coupler 28, actuation shaft 30, tubular guidewire member 34 (described below), and grouping coil 32 (described below) may be disposed within the lumen 25. These are just examples. The inner liner 14 may vary in form. For example, the inner liner 14 may include a single lumen, multiple lumens, or lack a lumen.

As described above, FIG. 2 and FIG. 3 illustrate the translation of translation members 24 in a distal-to-proximal direction (which shortens and radially expands the implant 16, as described above). However, FIG. 3 further illustrates that translation of the translation members 24 in a distal-to-proximal direction is accomplished by translation of the actuation shaft 30 and coupling member 28 within the lumen 25 of the inner catheter 14. For example, as the actuation shaft 30 is retracted (e.g., pulled proximally within lumen 25 of the inner catheter 14), it retracts the coupling member 28 proximally, which, in turn, retracts the translation members 24 in a proximal direction.

In some instances it may be desirable to maintain translation members 24 in a substantially linear configuration as they are translated within the lumen 25 of the inner catheter 14. In some examples, therefore, medical device system 10 may include a component designed to limit and/or prevent the translation members 24 from twisting around each other within the lumen 25 of the inner catheter 14. For example, FIG. 2 and FIG. 3 illustrate a grouping coil 32 wound around the translation members 24 such that the grouping coil 32 maintains the translation members 24 in a substantially liner configuration (and thereby limits and/or prevents the translation members 24 from twisting within lumen 25) as the translation members 24 are translated through the lumen 25 of the inner catheter 14.

FIG. 2 and FIG. 3 further illustrate that the proximal end of the grouping coil 32 may be positioned adjacent the distal end of the coupling member 28 and that the distal end of the grouping coil 32 may be positioned adjacent the distal end of the inner catheter 14. In particular, the distal end of the grouping coil 32 may be prevented from extending distally beyond the distal end of the inner catheter 14 by the containment fitting 29. In other words, the distal end of the grouping coil 32 may contact the containment fitting 29.

It can be further appreciated that the grouping coil 32 may be positioned within the lumen 25 of the inner catheter 14 such that the grouping coil 32 may elongate and shorten (e.g., a length of the grouping coil may adjust) within the lumen 25 of the inner catheter 14. For example, as the coupling member 28 is translated in a proximal direction (shown in FIG. 3 as compared to FIG. 2), the grouping coil 32 may elongate while continuing to group and/or contain the translation members 24 in a substantially linear configuration.

FIG. 2 and FIG. 3 further illustrate that the medical device system 10 may include a tubular guidewire member 34 extending within the lumen 25 of the inner catheter 14. The tubular guidewire member 34 may include a lumen which permits a guidewire to extend and translate therein. In other words, the medical device system 10 may be advanced to a target site within a body over a guidewire extending within the lumen of the tubular guidewire member 34. Further, the tubular guidewire member 34 may extend from the handle member 17, through the lumen 25 of the inner member 14, through the implant 16 and terminate at a nosecone 36.

As shown in FIG. 2 and FIG. 3, in some instances the inner catheter 14 may include an exoskeleton 40 disposed along the outer surface of the inner catheter 14. The exoskeleton 40 may be positioned between the outer member 12 and the inner catheter 14. For example, the exoskeleton 40 may be positioned between the inner surface of the outer member 12 and the outer surface of the inner catheter 14. Additionally, a distal end 42 of the exoskeleton 40 may be rigidly fixed with respect to the end region 26 of the inner member 14. In some examples, the distal end 42 of the exoskeleton 40 may be fixed directly to the inner member 14. In other examples, the exoskeleton 40 may be attached to a fitting (not shown) which is fixed directly to the inner member 14. In other instances, a containment fitting 29 (or other similar fitting) may be used to prevent the distal end 42 of the exoskeleton 40 from moving with respect to the end region 26 of inner member 14.

The exoskeleton 40 may include a plurality of discrete members or articulating links. For example, the exoskeleton 40 may include a plurality of bead members 41 and a plurality of barrel members 43. Other discrete members are contemplated that may have differing shapes and/or configurations. In general, the discrete members (e.g., the bead members 41 and the barrel members 43) are engaged with one another and are designed to increase the compression resistance, the tension resistance, or both of the inner catheter 14 while also affording a desirable amount of flexibility and kink resistance such that the inner catheter 14 can be navigated through the anatomy. The bead members 41 and the barrel members 43 may be arranged in a number of different configurations along the inner catheter 14. In at least some instances, the bead members 41 and the barrel members 43 alternate along the inner catheter 14. Other arrangements and/or patterns are contemplated.

It can be appreciated from the above discussion that the outer member 12, the inner shaft 14 (including the exoskeleton 40), the actuation shaft 30 (which is coupled to the translation members 24) and the tubular guidewire member 34 may all extend from a position adjacent the medical implant 16 to a position in which they enter the handle member 17. For example, FIG. 4 illustrates that the outer sheath 12, the inner shaft 14 (including the exoskeleton 40), the actuation shaft 30 (which is coupled to the translation members 24) and the tubular guidewire member 34 may extend from an example medical implant 16 (which may be similar in form and function to the medical implant described above) and enter the distal end 45 of the handle member 17.

In some instances it may be desirable to design medical device system 10 such that the inner member 14 has a different orientation with respect to outer member 12 than that shown in the illustrations of FIG. 2 and FIG. 3. For example, FIG. 4 illustrates the inner member 14 may be rotated 90 degrees as compared to the inner member 14 shown in FIG. 2 and FIG. 3. Further, rotation of the inner member 14 may also rotate the actuation shaft 30 and the tubular guidewire member 34 (positioned within lumen 25 of the inner member 14). For example, as shown in FIG. 4, the actuation shaft 30 and the tubular guidewire member 34 have been rotated 90 degrees (as compared to their configuration shown in FIG. 2 and FIG. 3), and therefore, the tubular guidewire member 34 can be conceptualized as being positioned "behind" the actuation shaft 30 in the illustration.

Figure 4:
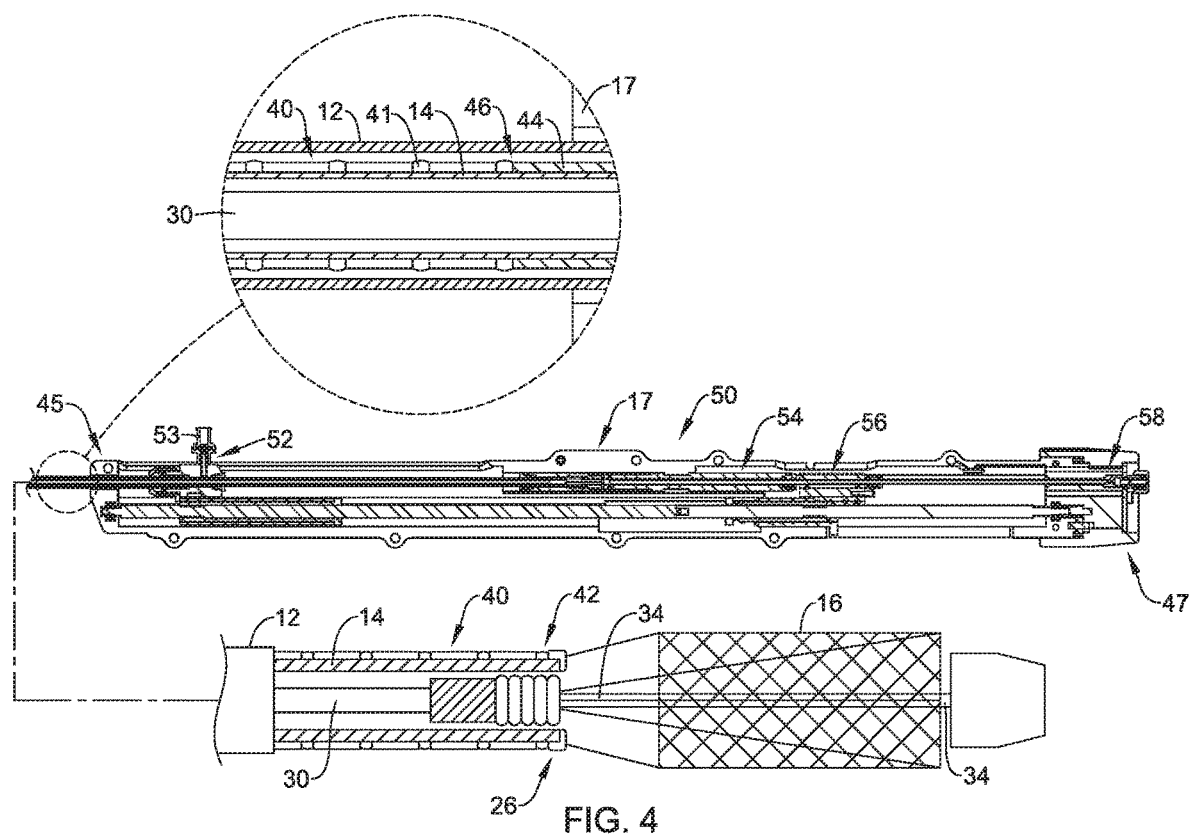
FIG. 4 is a partial cross-sectional view of a portion of an example medical device delivery system.

FIG. 4 further illustrates that in some examples the exoskeleton 40 (described above) may further include a hypotube 44 positioned over inner member 14. The hypotube 44 may be aligned with the alternating bead 41 and barrel 43 members of the exoskeleton 40. For example, in some instances the alternating bead 41 and barrel 43 components of the exoskeleton 40 may abut the hypotube 44 at a position which is distal to the distal end 45 of the handle member 17. In other words, the transition from the bead 41 and barrel 43 components of the exoskeleton 40 to the hypotube 44 may occur outside of handle member 17. Further, the detailed view of FIG. 4 shows that a distal end 46 of the hypotube 44 may be positioned adjacent to a bead or barrel component 41/43. In other words, the distal end 46 of hypotube 44 may directly engage (e.g., contact) a bead or barrel component 41/43 of the exoskeleton 40. As will be discussed in greater detail below, the hypotube 44 may extend into and terminate within the handle member 17.

It can be appreciated that actuation of the various components (e.g., the outer member 12, the inner shaft 14, the actuation shaft 30 and the tubular guidewire member 34) described above may occur via a variety of actuation mechanisms disposed in handle member 17. It can further be appreciated that the actuation mechanisms may function to move the various tubular components described above relative to one another. Further, each individual actuation mechanism may need to be fluidly sealed to prevent fluid leakage into portions thereof (including components residing therein) which may be damaged or contaminated by contact with fluid.

FIG. 4 illustrates an example fluid sealing assembly 50. Fluid sealing assembly 50 may include an outer sheath seal assembly 52, a turnbuckle seal assembly 54, an actuation member seal assembly 56 and a guidewire member seal assembly 58, each of which will be described in greater detail below. Outer sheath seal assembly 52 may include a luer lock flushing port 53. The luer lock flushing port 53 may include a check valve. It can be appreciated that each of the outer member 12, the inner shaft 14 (including portions of the exoskeleton 40), the actuation shaft 30 and the tubular guidewire member 34 may be coupled to one or more of the outer sheath seal assembly 52, the turnbuckle seal assembly 54, the actuation member seal assembly 56 and the guidewire member seal assembly 58.

Figure 5:
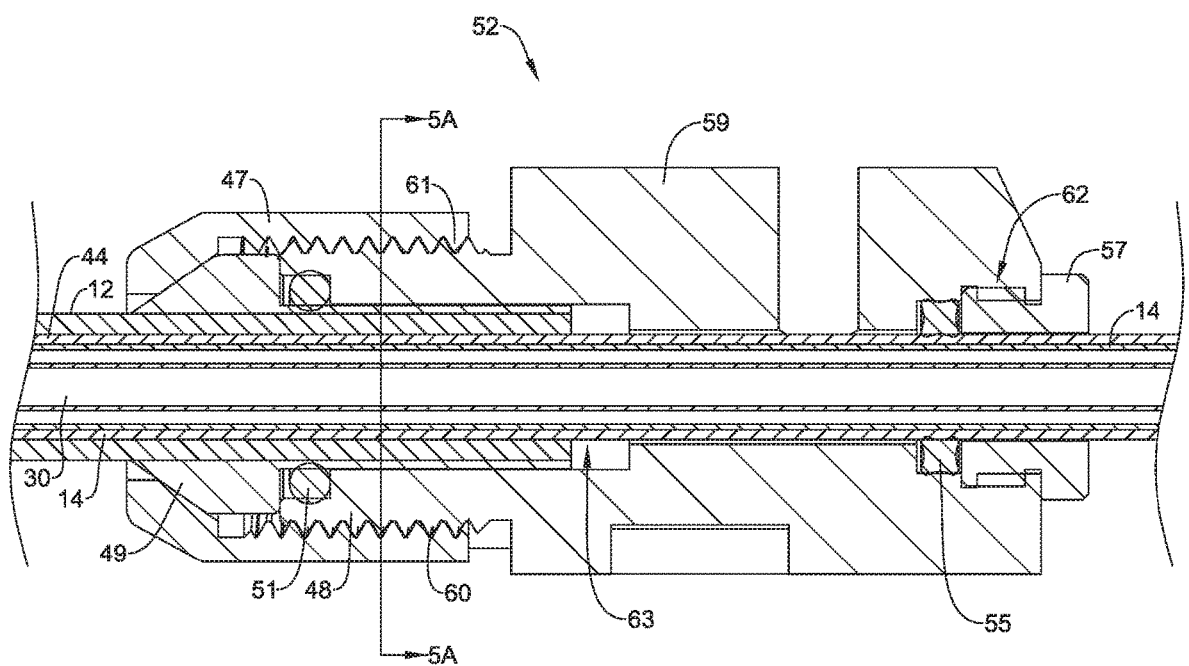
FIG. 5 is a partial cross-sectional view of a portion of an example medical device delivery system.

FIG. 5 illustrates an example outer sheath seal assembly 52. For clarity, luer lock flushing port 53 is removed from the outer sheath seal assembly 52 illustrated in FIG. 5. Additionally, outer sheath seal assembly 52 may include a body 59. Additionally, body 59 may include a post 48 extending along in a direction parallel to the longitudinal axis of the handle member 17. The post 48 may include a cavity 63 into which a proximal end of the outer member 12 may be inserted. Additionally, the post 48 of body 59 may include a threaded region 60.

Outer sheath seal assembly 52 may be designed to seal the outer member 12 while providing a passageway for the inner shaft 14, the hypotube 44, the actuation shaft 30 and the tubular guidewire member 34 (not visible in FIG. 5) to extend therethrough. For example, FIG. 5 illustrates that the outer sheath seal assembly 52 may include an outer seal 51. Outer seal 51 may be an O-ring or other similar type seal. As shown in FIG. 5, the outer seal 51 may be positioned between an inner surface of the post 48 of the body 59 and the outer surface of the outer member 12.

Additionally, the outer sheath seal assembly 52 may include a seal nut 47. Seal nut 47 may include a threaded region 61. It can be appreciated that the seal nut 47 may be designed to mate with the post 48. For example, it can be appreciated that the seal nut 47 may be designed to thread onto (e.g., screw onto) the post 48 of the body 59.

FIG. 5 further illustrates that in some examples, the outer member 12 may include a ferrule 49 which may be attached to the outer surface of the outer member 12. In some examples the ferrule 49 may be overmolded onto the outer surface of the outer member 12. As illustrated in FIG. 5, the profile of the outer surface of the ferrule 49 may be designed to mate with a portion of the inner surface of the seal nut 47. It can be further appreciated that the seal nut 47, the ferrule 49, the post 48 and the outer seal 51 may operate cooperatively to prevent fluid from leaking out of the outer sheath seal assembly 52. Specifically, rotation of the seal nut 47 onto the post 48 may translate the ferrule 49 in a distal-to-proximal direction, thereby compressing the outer seal 51 onto the outer surface of the outer member 12.

FIG. 5 further illustrates that the seal assembly 52 may include a threaded back-up ring 57. The back-up ring 57 may be threadably engaged with a mating threaded portion 62 of the body member 59. Threaded back-up ring 57 may be designed to compress a hypotube seal 55 onto the hypotube 44. For example, rotation of the back-up ring 57 onto the body 59 may compress the hypotube seal 55 onto the outer surface of the hypotube 44. In at least some examples, the hypotube seal 55 may be an X-ring type seal, however, other seal configurations are contemplated. Utilizing an X-ring seal design for the hypotube seal 55 may reduce frictional forces upon the hypotube 44 in instances when the hypotube 44 is translated through the hypotube seal 55.

It can be appreciated from the illustration in FIG. 5 and the above discussion that the outer member 12 may terminate within the outer sheath seal assembly 52. Accordingly, it can be further appreciated that actuation of the outer sheath seal assembly 52 may actuate (e.g., shift, translate, move, etc.) the outer sheath 12. While not expressly depicted in the figures, it can be appreciated that the handle 17 may include one or more actuation mechanisms designed to actuate the outer sealing assembly 52, which may shift outer member 12 relative to the hypotube 44, the inner member 14, the actuation shaft 30 and the tubular guidewire member 34. Actuation of the outer member 12 may uncover (e.g., partially deploy) the medical device 16 as described above.

Figure 5A:
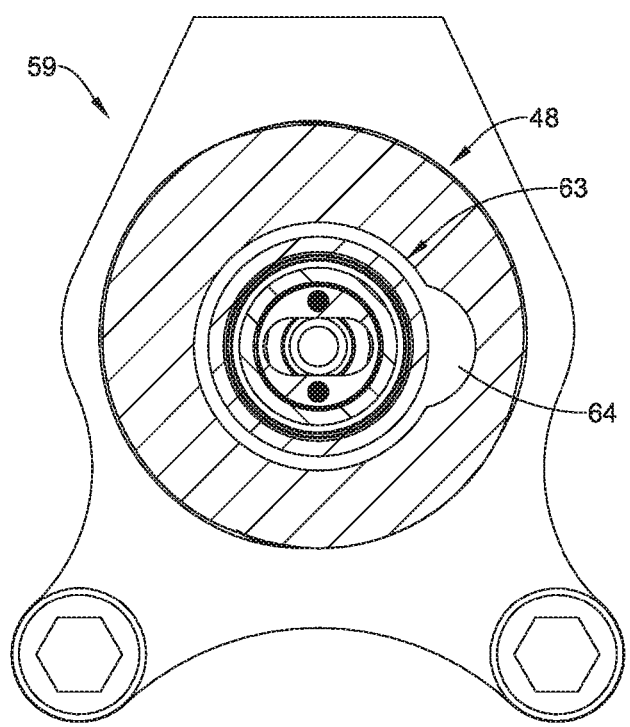
FIG. 5A is a partial cross-sectional view of a portion of an example medical device delivery system along line 5A-5A of FIG. 5.
Figure 5B:
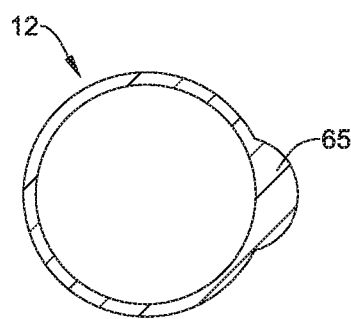
FIG. 5B is a partial cross-sectional view of a portion of an example medical device delivery system.

In some examples, the outer member 12 of the medical device system 10 may include one or more features which are designed to orient the outer member 12 with the handle 17 in a specific configuration. For example, FIG. 5A illustrates a cross-section of the body 59 of an example sealing assembly 52, as discussed above. The body 59 may be similar in form and function the body 59 discussed above. As discussed above, the post 48 may include a cavity 63 designed to accept the proximal end of an example outer member 12 therein. As shown in FIG. 5A, the cavity 63 may include an alignment recess 64, which, along with the overall profile of the cavity 63, is designed to align the curved portion 13 (shown in FIG. 1) of the outer member 12 with the body 59 (which, in turn, is ultimately aligned with the handle 17). Additionally, FIG. 5B shows a cross-section of the proximal end region of an example outer member 12. FIG. 5B shows the outer member 12 may include a rib 65 molded onto the outer surface of the outer member 12. It can be appreciated that the rib 65 may be aligned with the curved portion 13 of outer member 12. It can further be appreciated that the cross-sectional profile of the proximal end of the outer member 12 matches (e.g., mates with) the profile of cavity 63 (which includes alignment recess 64), discussed above.

Figure 6:
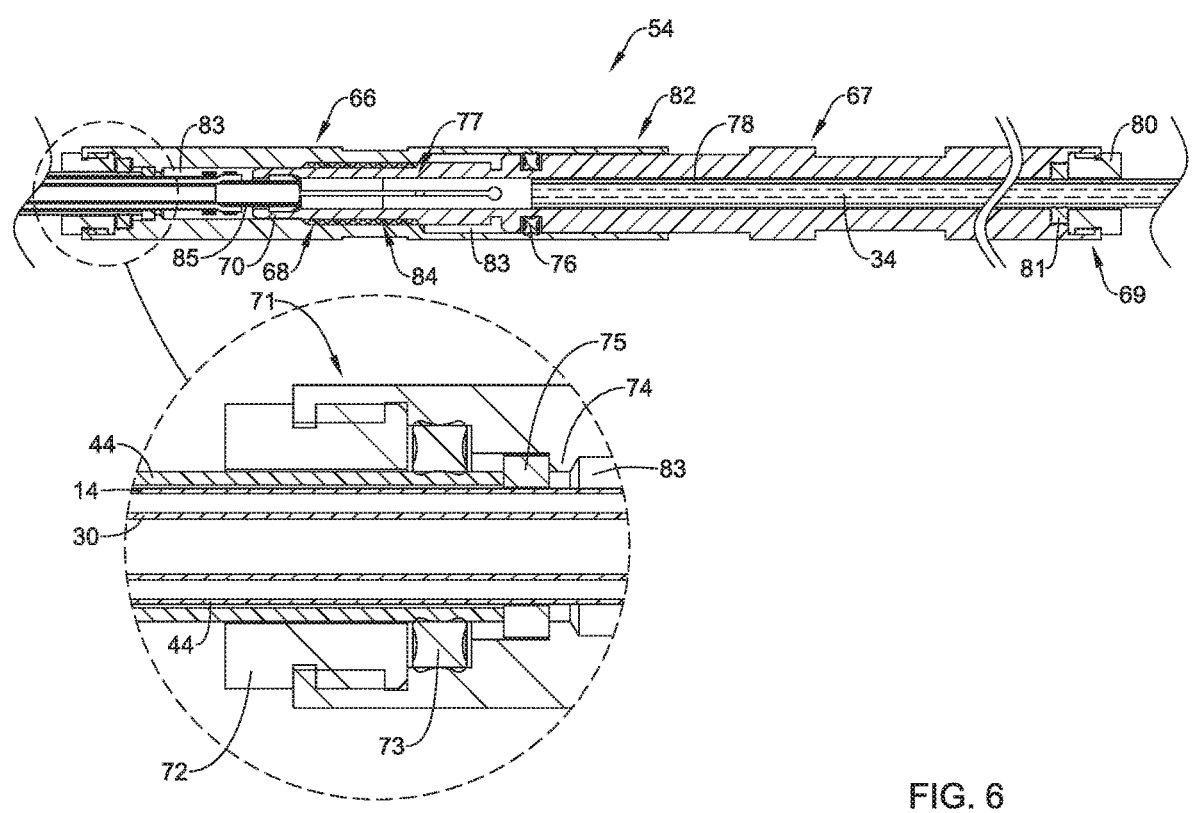
FIG. 6 is a partial cross-sectional view of a portion of an example medical device delivery system.

FIG. 6 illustrates an example turnbuckle seal assembly 54. The turnbuckle seal assembly 54 may include a cap member 66 coupled to a stationary member 67. Stationary member 67 may fixed relative to the handle member 17. In other words, the stationary member 67 may include one or more features that engage with handle 17, thereby preventing the stationary member 67 from moving with respect to the handle 17.

The cap member 66 may include a distal end 71 and a proximal end 82. Further, the cap member 66 may include a lumen 83 extending through a portion or the full length of the cap member 66. Further, the stationary member 67 may include a distal end 68 and a proximal end 69. As shown in FIG. 6, the distal end 68 of the stationary member 67 may be inserted into the lumen 83 of the cap member 66. Additionally, the stationary member 67 may include one or more threads which are designed to mate with one or more threads positioned within the lumen 83 of the cap member 66. The engagement of the threaded portion of the stationary member 67 and the threaded portion of the cap member 66 is shown in FIG. 6 as a threaded region 84. As will be discussed in greater detail below, it can be appreciated that if the stationary member 67 remains fixed with respect to the handle 17, rotation of the cap member 66 with respect to the stationary member 67 may translate cap member 66 proximally or distally (depending on the direction of rotation of cap member 66).

As shown in FIG. 6, the turnbuckle seal assembly 54 may include a first turnbuckle seal 76 positioned between the cap member 66 and the stationary member 67. In at least some examples, the first turnbuckle seal 76 may be an X-ring type seal, however, other seal configurations are contemplated.

The distal region 68 of the stationary member 67 may include one or more attachment fingers 70. Attachment fingers 70 may be coupled to a proximal end of the inner member 14 (the inner member 14 is shown in FIG. 6 extending into the lumen 83 of the cap member 66). In at least some examples, the attachment fingers 70 of the stationary member 67 may be engaged with a fitting 85 disposed along the proximal end of the inner member 14.

It can be appreciated that because the stationary member 67 is fixed with respect to handle 17 and that the inner member 14 is engaged to the stationary member 67 (via the fitting 85 and attachment fingers 70), that the inner member 14 may be fixed with respect to the handle 17. Accordingly, it can be further appreciated from the above discussion that rotation of the cap member 66 may translate the cap member 66 proximally or distally relative to the inner member 14.

FIG. 6 further illustrates that the hypotube 44 may extend into and terminate within the cap member 66. Further, FIG. 6 shows that the proximal end of the hypotube 44 may include a hypotube fitting 75. The hypotube fitting 75 may be securely fixed to the proximal end of the hypotube 44. Additionally, FIG. 6 shows that the hypotube fitting 75 may engage with a protrusion 74 extending radially inward from the surface of the cap member 66. It can further be appreciated that rotation of the cap member 66 may translate the hypotube 44 in a proximal-to-distal direction. The translation of the hypotube 44 in a proximal-to-distal direction may also translate the distal end 46 of the hypotube 44 (shown in the detailed view of FIG. 4).

Further, as discussed above, the distal end of the hypotube 44 may be engaged with the bead and barrel components 41/43 of exoskeleton 40. The distal end of the bead and barrel components 41/43 may be fixed to the distal end region of inner member 14 (discussed above with respect to FIG. 4). Therefore, proximal-to-distal movement of the hypotube 44 (via rotation of the cap member 66) may compress the individual bead and barrel components 41/43 against one another along the outer surface of the inner member 14. Additionally, it can be further appreciated that putting the exoskeleton 40 in compression may correspondingly place the inner member 14 (and components thereof) in tension.

FIG. 6 further illustrates that the actuation shaft 30 and the tubular guidewire member 34 (not shown, but understood as being positioned "behind" the actuation shaft 30 in the illustration) may enter the distal end 71 of the cap member 66. For simplicity purposes, FIG. 6 illustrates the actuation shaft 30 and the tubular guidewire member 34 may engage and be coupled together via a coupling component 77 of the turnbuckle seal assembly 54. The coupling component 77 is designed to couple the actuation shaft 30, the tubular guidewire member 34 and the actuation hypotube 78 together while permitting the tubular guidewire member 34 to extend through at least a portion of the actuation hypotube 78. For example, FIG. 6 illustrates the tubular guidewire member 34 (depicted as dashed lines) extending within at least a portion of the actuation hypotube 78 (which is coupled to a proximal end of the coupling component 77).

Similarly to that discussed with respect to the outer sealing assembly 52 above, the distal region 71 of the turnbuckle sealing assembly 54 may include a threaded back-up ring 72. Back-up ring 72 may be threadably engaged with a mating threaded portion (not shown in FIG. 6) of cap member 66. Threaded back-up ring 72 may be designed to compress a second turnbuckle seal 73 onto the hypotube 44. For example, rotation of the back-up ring 72 may compress the second turnbuckle seal 73 onto the outer surface of the hypotube 44. In at least some examples, the second turnbuckle seal 73 may be an X-ring type seal, however, other seal configurations are contemplated. Utilizing an X-ring seal design for the second turnbuckle seal 73 may reduce frictional forces upon the hypotube 44 in instances when the hypotube 44 is translated through the second turnbuckle seal 73.

Additionally, the proximal region 69 of the stationary member 67 may include a second threaded back-up ring 80. The second back-up ring 80 may be threadably engaged with a mating threaded portion (not shown in FIG. 6) of the stationary member 67. Threaded back-up ring 80 may be designed to compress a third turnbuckle seal 81 onto the actuation hypotube 78. For example, rotation of the back-up ring 80 may compress the third turnbuckle seal 81 onto the outer surface of the actuation hypotube 78. In at least some examples, the third turnbuckle seal 81 may be an X-ring type seal, however, other seal configurations are contemplated. Utilizing an X-ring seal design for the third turnbuckle seal 81 may reduce frictional forces upon the actuation hypotube 78 in instances when the actuation hypotube 78 is translated through the third turnbuckle seal 81.

Figure 7:
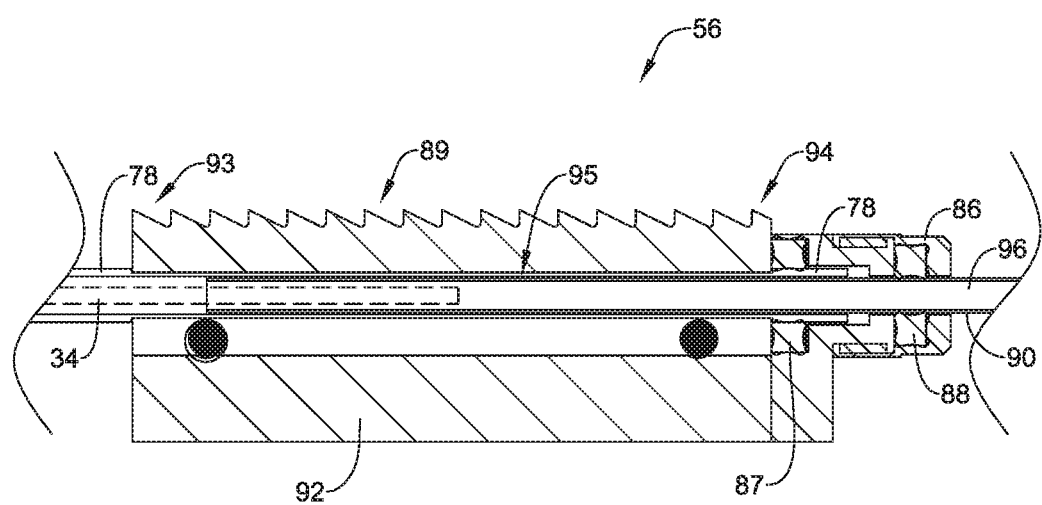
FIG. 7 is a partial cross-sectional view of a portion of an example medical device delivery system.

FIG. 7 illustrates the actuation member sealing assembly 56. The actuation sealing assembly 56 may include a block member 92. The block member 92 may include a distal end 93, a proximal end 94 and a lumen 95 extending therethrough. As illustrated in FIG. 7, the actuation hypotube 78 may enter the lumen 95 at the distal end 93 of the block member 92. Further, the actuation hypotube 78 may extend through the lumen 95 of block member 92 and terminates in a threaded back-up ring 86.

Similar to that described above, the back-up ring 86 utilized in the actuation member seal assembly 56 may be threadably engaged with a mating threaded portion (not shown in FIG. 7) of block member 92. The threaded back-up ring 86 may be designed to compress a first actuation seal 87 onto the actuation hypotube 78. For example, rotation of the back-up ring 86 may compress the first actuation seal 87 onto the outer surface of the actuation hypotube 78. In at least some examples, the first actuation seal 87 may be an X-ring type seal, however, other seal configurations are contemplated. Utilizing an X-ring seal design for the first actuation seal 87 may reduce frictional forces upon the actuation hypotube 78 in instances when the actuation hypotube 78 is translated through the third turnbuckle seal 81.

As discussed above, the actuation hypotube 78 may be coupled to the actuation shaft 30 and the tubular guidewire member 34 via coupling component 77. Further, the actuation shaft 30 may be coupled via coupler 28 (shown in FIG. 2 and FIG. 3) to the translation members 24 while the tubular guidewire member 34 may be coupled to the nosecone 36. Therefore, it can be appreciated that actuation of block member 92 (and, correspondingly, the actuation hypotube 78 which is also coupled to the coupling component 77) in a distal-to-proximal direction may actuate both the translation members 24 and the nosecone 36 in a distal-to-proximal direction. As discussed above, the distal-to-proximal movement of the translation members 24 may shift the implant 16 from its length "$L_1$" illustrated in FIG. 2 to its length "$L_2$" illustrated in FIG. 3.

In some instances, the distal-to-proximal movement of the block member 92 may be controlled via an actuation handle (not shown in FIG. 7). The actuation handle may include a pawl spring (not shown) that may engage a plurality of teeth 89 positioned along an outer surface of block member 92. Engagement of the pawl spring with the plurality of teeth 89 may permit the block member 92 to shift in a distal-to-proximal direction while also preventing the block member 92 from shifting in a proximal-to-distal direction.

FIG. 7 further illustrates that the actuation member sealing assembly 56 may further include a guidewire hypotube 90. The guidewire hypotube 90 may enter the lumen 95 of the block 92 at the distal end 93 of the block member 92. The guidewire hypotube 90 may be a stationary hypotube. In other words, in some examples the guidewire hypotube 90 may rigidly fixed relative (e.g., remain in a fixed position) relative to the block 92 and the handle member 17. A second actuation seal 88 may be positioned within the back-up ring 86. The threaded back-up ring 86 may be designed to compress the second actuation sealing 88 onto the proximal guidewire tube 90.

Additionally, it can be appreciated that the guidewire hypotube 90 may extend into a lumen (not shown in FIG. 7) of the actuation hypotube 78. Therefore, it further be appreciated that as the block member 92 is actuated (as discussed above), the actuation hypotube 78 may travel along the outer surface of the guidewire hypotube 90. Additionally, the tubular guidewire member 34 may terminate at a position within the lumen of the guidewire hypotube 90. For example, FIG. 7 illustrates the tubular guidewire member 34 (depicted by dashed lines in FIG. 7) terminating in the lumen 96 of the guidewire hypotube 90.

Figure 8:
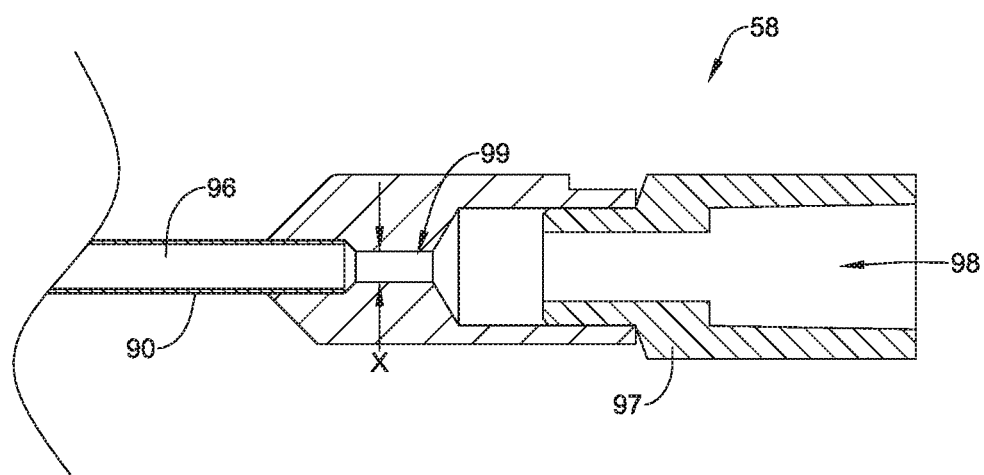
FIG. 8 is a partial cross-sectional view of a portion of an example medical device delivery system.

FIG. 8 illustrates the guidewire tubing sealing assembly 58. The guidewire sealing assembly 58 may include a threaded luer lock port 97. The luer lock port 97 may be rigidly fixed to the handle member 17. Further, the luer lock port 97 may include a lumen 98 extending therethrough.

As illustrated in FIG. 8, the luer lock port 97 may be attached to the proximal guidewire tube 90, which extends distally from the block 92 of the actuation member seal assembly 56, described above with respect to FIG. 7. In some examples, the proximal guidewire tube 90 may be welded (e.g., hermetically welded) to a portion of the luer lock port 97.

Additionally, it can be appreciated from FIG. 8 that the lumen 98 of the luer lock port 97 may be in fluid communication with the lumen 96 of the proximal guidewire tube 90. This fluid communication path may permit a guidewire (not shown) to be inserted through the luer lock port 97 and into the lumen 96 of the proximal guidewire tube 90. Additionally, FIG. 8 illustrates the actuation seal member assembly 56 including a guidewire sealing channel 99 having a diameter depicted as "X." It can be appreciated that in at least some examples, the diameter "X" may be designed to permit a guidewire to pass therethrough while also providing minimum clearance such that fluid is not permitted to pass therethrough. In other words, the clearance between the outer diameter of a guidewire (not shown) and the diameter "X" of the channel 99 may be designed to prevent fluid from leaking out of the luer lock port 97.

The materials that can be used for the various components of the medical devices and/or system 10 disclosed herein may include those commonly associated with medical devices. However, this is not intended to limit the devices and methods described herein, as the discussion may be applied to other components of the medical devices and/or systems 10 disclosed herein including the various shafts, liners, components described relative thereto.

The medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MRI) compatibility is imparted into the medical device 10. For example, the medical device 10 may include a material that does not substantially distort the image and create substantial artifacts (e.g., gaps in the image). Certain ferromagnetic materials, for example, may not be suitable because they may create artifacts in an MRI image. The medical device 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A system for delivering an implantable medical device, comprising:
    a handle member including a seal assembly, wherein the seal assembly is disposed within the handle member, and wherein the seal assembly includes:
        a turnbuckle assembly including a stationary member and a cap coupled to the stationary member;
    wherein the stationary member is coupled to an inner member;
    wherein the cap is coupled to an exoskeleton that includes a plurality of discrete segments engaged with one another disposed along an outer surface of the inner member; and
    wherein the cap is designed to shift distally relative to the stationary member whereupon the exoskeleton is put in compression.

2. The system of claim 1, wherein the cap is threadedly engaged with the stationary member.

3. The system of claim 1, further comprising a hypotube positioned along the inner member, wherein the hypotube is positioned between the cap and the exoskeleton.

4. The system of claim 3, wherein the cap includes a protrusion configured to engage a proximal portion of the hypotube.

5. The system of claim 3, wherein the cap includes a first seal, and wherein the first seal is disposed along an outer surface of the hypotube.

6. The system of claim 1, wherein the stationary member includes a distal tip region configured to engage a proximal portion of the inner member.

7. The system of claim 1, wherein the stationary member includes a recessed region, and wherein the recessed region is designed to mate with a protrusion in the handle member.

8. The system of claim 1, wherein the stationary member is configured to prevent the inner member from shifting with respect to the handle member.

9. A system for delivering an implantable medical device, comprising:
    a deployment sheath;
    an inner member disposed within a portion of the deployment sheath; and
    a handle coupled to the deployment sheath, wherein the handle includes a seal assembly disposed within the handle, and wherein the seal assembly includes:
        a first actuating assembly, wherein the first actuating assembly is configured to receive the deployment sheath;

a second actuating assembly, wherein the second actuating assembly is configured to receive an actuating shaft; and a turnbuckle assembly including a cap and a stationary member;

wherein the turnbuckle assembly is configured to compress an exoskeleton positioned along the inner member.

10. The system of claim 9, wherein the cap is designed to shift distally with respect to the stationary member.

11. The system of claim 10, wherein the exoskeleton includes a plurality of discrete segments engaged with one another, and wherein shifting the cap distally compresses the exoskeleton together.

12. The system of claim 10, wherein the cap is threadedly engaged with the stationary member.

13. The system of claim 11, further comprising a hypotube positioned along the inner member, wherein the hypotube is positioned between the cap and the exoskeleton.

14. The system of claim 13, wherein the cap includes a protrusion configured to engage a proximal portion of the hypotube.

15. The system of claim 13, wherein the cap includes a first seal, and wherein the first seal is disposed along an outer surface of the hypotube.

16. The system of claim 10, wherein the stationary member includes a distal tip region configured to engage a proximal portion of the inner member.

17. The system of claim 10, wherein the stationary member includes a recessed region, and wherein the recessed region is designed to mate with a protrusion in the handle.

* * * * *